United States Patent
Chiari

(10) Patent No.: US 9,834,617 B2
(45) Date of Patent: *Dec. 5, 2017

(54) METHOD FOR IMMOBILIZING BIOLOGIC MOLECULES ON SOLID SURFACES

(71) Applicant: Marcella Chiari, Milan (IT)

(72) Inventor: Marcella Chiari, Milan (IT)

(*) Notice: Subject to any disclaimer, the term of this patent is extended or adjusted under 35 U.S.C. 154(b) by 0 days.

This patent is subject to a terminal disclaimer.

(21) Appl. No.: 14/454,541

(22) Filed: Aug. 7, 2014

(65) Prior Publication Data

US 2015/0087555 A1    Mar. 26, 2015

Related U.S. Application Data

(63) Continuation of application No. 10/536,306, filed as application No. PCT/EP02/13513 on Nov. 29, 2002, now Pat. No. 8,809,071.

(51) Int. Cl.
| | |
|---|---|
| *C07K 17/08* | (2006.01) |
| *B01J 19/00* | (2006.01) |
| *G01N 33/531* | (2006.01) |
| *G01N 33/543* | (2006.01) |
| *C08F 220/56* | (2006.01) |
| *C08F 220/60* | (2006.01) |
| *C08F 226/06* | (2006.01) |
| *C09D 139/04* | (2006.01) |
| *C08F 220/32* | (2006.01) |

(52) U.S. Cl.
CPC ........... *C07K 17/08* (2013.01); *B01J 19/0046* (2013.01); *C08F 220/56* (2013.01); *C08F 220/60* (2013.01); *C08F 226/06* (2013.01); *C09D 139/04* (2013.01); *G01N 33/531* (2013.01); *G01N 33/54353* (2013.01); *B01J 2219/00608* (2013.01); *B01J 2219/00637* (2013.01); *C08F 220/32* (2013.01)

(58) Field of Classification Search
CPC .... C08F 220/56; C08F 220/60; C08F 226/06; C08F 220/32; G01N 33/531; G01N 33/54353; B01J 19/0046; B01J 2219/00608; B01J 2219/00637; C07K 17/08; C09D 139/04

See application file for complete search history.

(56) References Cited

U.S. PATENT DOCUMENTS

| | | |
|---|---|---|
| 4,035,330 A | 7/1977 | Schultz |
| 5,202,227 A | 4/1993 | Matsuda et al. |
| 5,858,653 A | 1/1999 | Duran et al. |
| 5,861,247 A | 1/1999 | Mirzabekov et al. |
| 5,932,711 A | 8/1999 | Boles et al. |
| 5,981,734 A | 11/1999 | Mirzabekov et al. |
| 6,121,027 A | 9/2000 | Clapper et al. |
| 6,180,770 B1 | 1/2001 | Boles et al. |
| 6,406,845 B1 | 6/2002 | Walt et al. |
| 6,762,019 B2 | 7/2004 | Swan et al. |
| 8,809,071 B2 | 8/2014 | Chiari |
| 2002/0115740 A1 | 8/2002 | Beuhler et al. |

FOREIGN PATENT DOCUMENTS

| | | |
|---|---|---|
| WO | WO 01/002452 | 1/2001 |
| WO | WO 01/066554 | 9/2001 |

OTHER PUBLICATIONS

Chiari et al., "A new absorbed coating for DNA fragment analysis by capillary electrophoresis", Electrophoresis 2000, vol. 21, pp. 1521-1526.

Nguyen et. al., "Syntheses and applications of water-soluble reactive polymers for purificaiton and immobilization of biomolecules", Biotechnology and Bioengineering 1989, vol. 34, pp. 1186-1190.

Pollak et al., "Enzyme immobilization by condensation copolymerization in cross-linked polyacrylamide gels", J. Am. Chem. Soc. ,1980, vol. 1 02, No. 20, pp. 6324-6336.

Doherty et al., "Critical factors for high-performance physically adsorbed (dynamic) polymeric wall coatings for capillary electrophoresis of DNA", Electrophoresis (2002), 23, pp. 2766-2776.

Madabhushi, Ramakrishna., "Separation of 4-color DNA sequencing extension products in noncovalently coated capillaries using low viscosity polymer solutions", Electrophoresis (1998), 19, pp. 224-230.

Timofeev et al., "Regioselective Immobilization of Short Oligonucleotides to Acrylic Copolymer Gels", Nucleic Acid Research, (1996), 24, 16, pp. 3142-3148.

*Primary Examiner* — Shafiqul Haq
(74) *Attorney, Agent, or Firm* — The Marbury Law Group, PLLC

(57) ABSTRACT

The invention provides a method for immobilization of biological molecules such as nucleic acids, peptides and proteins onto the surface of a glass or plastic solid support.

19 Claims, 5 Drawing Sheets

METHOD FOR IMMOBILIZING BIOLOGIC MOLECULES ON SOLID SURFACES

The present invention relates to a method to attach biological molecules, such as oligonucleotides, peptides and proteins onto the surface of a glass or plastic support. The immobilization of biological molecules onto different substrates plays a crucial role in the development of the DNA microarray technology (Nature Genetics Supplement Vol 21, 1999). In recent years, the DNA microarray technology is gaining increasing acceptance in different areas of biomedical analysis. The technique, thanks to its versatility and miniaturization, has determined a considerable advancement in the sensitivity and throughput of different analysis. The coating methods used in the production of microarray slides represent a key factor for the success of the technique. Over the last few years, polymeric coatings have been developed based on polyacrylamide or polydimetylacrylamide gels for regioselective immobilization by the 3' or 5' end of oligonucleotides. A procedure for immobilizing DNA in polyacrylamide and dimethylacrylamide gels was developed by the Mirzabekov group at the Engelhardt Institute of Moscow (U.S. Pat. No. 0,981,734). The method consists of introducing functional groups onto a suitable polymeric support.

U.S. Pat. No. 5,861,247 discloses a method for constructing oligonucleotide matrices, which comprises confining a light sensitive fluid to a surface, exposing said light-sensitive fluid to a light pattern so as to cause the fluid exposed to the light to coalesce into discrete units and adhere to the surface and contacting each of the units with a set of different oligonucleotide molecules so as to allow the molecules to disperse into the units. The procedure to fix a regular set of polyacrylamide gel pads on a glass slide is cumbersome as it involves silanization of the glass and photopolymerization of acrylamide.

In another approach, Boles and coworkers at the Mosaic Technologies Inc. (U.S. Pat. No. 5,932,711 and U.S. Pat. No. 6,180,770) have developed chemistry for solid phase attachment of oligonucleotides based on the synthesis of oligonucleotides bearing 5'-terminal acrylamide modifications. Oligonucleotides bearing polymerizable functions are copolymerized with acrylamide/bisacrylamide and covalently attached to an organosilane surface to which acryloyl groups have previously been grafted. Also this procedure is time consuming and requires a careful control of operative parameters.

U.S. Pat. No. 6,121,027 discloses a process for the production of poly-, difunctional reagents having a polymeric backbone, one or more pendent photoreactive moieties, and two or more pendent bioactive groups. The reagent can be activated to form a bulk material or can be brought into contact with the surface of a previously formed biomaterial and activated to form a coating. The pendent bioactive groups function by promoting the attachment of specific nucleic acids and other molecules that are capable of binding noncovalently to specific and complementary portions of molecules.

U.S. Pat. No. 5,858,653 discloses a method to produce a polymeric support for oligonucleotide and DNA attachment. In this patent, a variety of homopolymers and copolymers resulting from addition or condensation polymerization provide a polymeric backbone capable of bearing ionic groups, photogroups and thermodynamically reactive groups. The method is based on the activation of latent photoreactive groups to generate active species which undergo addition to other active species on the same or on another molecule in such a way that a tridimensional network is generated in which reactive functions are properly spaced from the surface. Although very flexible, also this method involves the synthesis of complex copolymers whose composition may be difficult to be controlled.

Object of the present invention is a simple and fast method for immobilizing biological molecules such as peptides, proteins and nucleic acids onto the surface of glass or plastic materials commonly used as substrates for the adhesion of said molecules, such as microwell plates, beads, tubes, microscope slides, silicon wafers and membranes. Suitable plastic materials are, for instance, made of polystyrene, polycarbonate, polyvinylchloride and polypropylene. The method of the invention exploits the ability of some copolymers of N-substituted polyacrylamides to be adsorbed onto the surface of the above mentioned materials, and, in some cases, once absorbed, to covalently react with the surface through appropriate functional groups, forming a highly hydrophilic coating with accessible functionalities. The coating bears reactive groups able to covalently bind the biological molecules of interest.

The polymers object of the present invention are obtained through radical polymerization of a mixture comprising a) a monomer selected from the group comprising acrylamide, methacrylamide, preferably mono- or di-substituted on the nitrogen by C1-C12 liner or branched alkyl chains, which in turn can be substituted by a halogen, preferably fluorine, or by a methoxy group or, in the case of N-mono substituted compounds, by a hydroxy group;

b) an ethylene or acrylic monomer linked by means of C1-C6 alkyl chains optionally interrupted by O, N or S atoms, to functional groups able to covalently react with amines, thiols or hydroxyls present on a protein/peptide, or with the amino-modified residue of a nucleic acid, wherein said functional groups are preferably succinimide, oxiranes, carboxylic acids;

and, optionally, c) an ethylene monomer bearing groups able to covalently react with the glass silanols, preferably epoxy functions, d) an ethylene monomer carrying an ionizable group which assumes a positive charge in aqueous solution, preferably ammonium groups.

The content of monomer (b) in the polymerization mixture is from 0.1 to 25% w/v, preferably 1-4%, the remaining part being constituted by monomer (a). The content of monomers (c) and (d) can be up to 25% w/v, preferably 1-4% for monomer (c) and 5-10% for monomer (d). Monomer (d) cooperates with monomer (c) to increase the adhesion of the polymeric coating and thus of biological molecules to the support by combining covalent and electrostatic interactions.

Examples of groups able to covalently bind biological molecules are carboxylic acids active esters, optionally substituted 4- or 5-membered cyclic carboxyimides, such as optionally substituted succinimide and maleimide and oxirane. Such groups can be already present in one or more monomer of the starting polymerization mixture or they can be introduced after polymerization (Timofeev et al., Nucleic Acid Research, 1996, 24, 16, 3142-3148). Examples of groups able to electrostatically interact with biological molecules are amino and quaternary ammonium groups.

Preferred monomers according to the invention are N,N-dimethyl acrylamide (monomer (a)); allyl oxyalkyl(C1-C4) oxiranes, N-acryloyloxy succinimide or N-acryloyloxyalkyl (C1-C4)succinimide, and acryloyl carboxy acids in which the carboxy group is spaced from the acryloyl residue by a C1-C5 alkyl chain (monomers (b)), allyl oxymethyl oxirane and N-acryloyloxysuccinimide being particularly preferred; glycidyl methacrylate (methacrylic acid 2,3-epoxypropyl ester) and allyl glycidyl ether (allyl 2,3-epoxypropyl ether) (monomers (c)); N,N,N,-trimethyl aminoethylacrylamide (monomer (d)).

Preferred polymers are obtained from the following monomeric mixtures:
a) N,N-dimethylacrylamide and N-acryloyloxysuccinimide ((a)+(b));
b) N,N-dimethylacrylamide, N-acryloyloxysuccinimide and N,N,N-trimethylaminoethylacrylamide ((a)+(b)+(d));
c) N,N-dimethylacrylamide, acrylic acid, glycidylmethacrylate ((a)+(b)+(c)).

The polymerization reaction can be carried out in apolar organic solvents, preferably tetrahydrofuran, and is usually catalyzed by radicalic catalizers, such as α,α'-azoisobutyronitrile (AIBN). When using polymers such as N,N-dimethylacrylamide, glycidyl methacrylate, acrylic acid ((a)+(b)+(c)), the polymerization reaction is carried out in water using ammonium persulfate and tetraethylenemethylenediamine (TEMED) as catalysts. According to the invention, the above mentioned polymers are adsorbed on the substrate surface by contacting an aqueous solution containing them with said surface for a time that can vary depending on the mixture used and the surface to treat, but that will usually range from a few seconds to 30 min and more, so as to form a highly hydrophilic coating in which the reactive functions or groups are accessible to the biological molecules. Afterwards, in case the monomer able to bind the biological molecules has to be activated in situ, either the acid will be transformed into the reactive ester or the protein molecule or modified DNA will be directly coupled in the presence of a dehydrating agent such as dicyclohexylcarbodiimide or diisopropylcarbodiimide. When the monomer is already activated in the polymer, before adsorption, proteins and modified DNA will be directly linked covalently to said reactive groups, according to known procedures (DNA Microarrays A Practical Approach, Mark Schena Ed., Oxford University Press). The aqueous solutions used for the deposition of the polymeric coating have a polymer content ranging from 0.1 to 20% w/v, preferably from 0.1. to 1% w/v. In a preferred embodiment, the aqueous solution contains 20% saturation ammonium sulfate.

The affinity for the substrate is such that the polymers adsorption generates a coating which cannot be removed from the substrate surface by the usual buffers, even in the presence of additives such as urea, SDS, salts or at high temperature. In particular, polymers containing epoxy groups are attached to the glass by a mixed adsorption/covalent mechanism. The presence of covalent binding sites further stabilizes the coating.

According to a preferred embodiment of the invention, polymers are used for coating DNA microarrays, peptides or proteins, which can be used in hybridization techniques with complementary molecules. Examples of complementary moleculesare antigen/antibody, ligand/receptor, enzyme/substrate, protein/protein, preferably nucleic acid molecules that can be used in hybridization techniques according to well established procedures. The invention also comprises substrates of plastic or glassy materials, such as microwell plates, beads, tubes, microscope slides, silicon wafers and membranes, coated with the polymers herein described.

Figure 1:
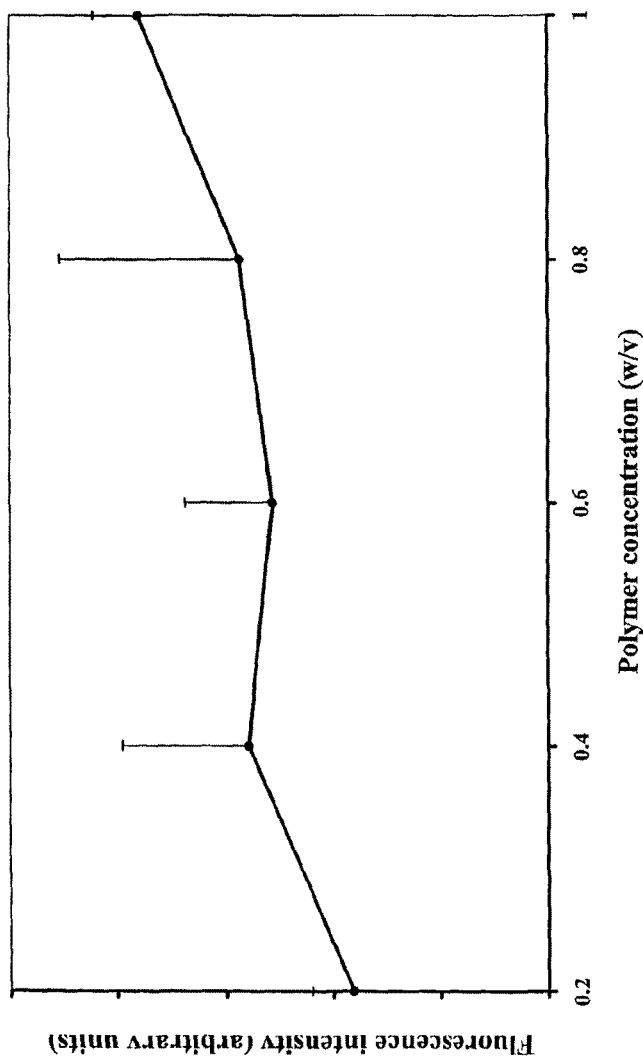
FIG. 1: Fluorescence signals of hybridized oligonucleotides as a function of the polymer concentration used for the coating. One nL of 5'-amino modified oligonucleotide, 50 µM (femtomol/nanoliter), was spotted on a glass slides coated with ammonium sulfate solutions of (DMA98-co-NAS2) at concentration 0.2, 0.4, 0.6, 0.8 and 1% w/v. The spotted oligonucleotides were hybridized according to the protocol reported in the example section with a target complementary oligonucleotide labeled at the 3' end with Cy5 for 2 hours at 65° C. After washing, the slides were scanned with a Virtek scanner, and the images were analyzed using the Virtek ChipReader software. Each value represents the average fluorescence intensity value of six spots given in arbitrary units.

A 5' amino-modified oligo corresponding to a fragment of neomycin gene from plasmid pEGFP-N1, in concentration 3.125, 6.25, 12.5, 25 and 50 µM (from left to right) was spotted and hybridized, according to the procedure described in the Examples, for 2 hours at 42° C., with the cDNA complementary fragment labeled at the 3' end with Cy5. After washing, the slides were scanned with a Virtek scanner, and the images were analyzed using the Virtek ChipReader software.

The following examples illustrate in detail the invention.

EXAMPLE 1

Synthesis of N-acryloyloxysuccinimide

To a solution of N-hydroxysuccinimide (NAS) (1.15 g, 10.0 mmol) and triethylamine (1.53 ml) in chloroform (15 ml), acryloyl chloride (0.99 g, 11.0 mmol), cooled at 0° C., was added dropwise, under mechanical stirring, over a period of 30-min. After an additional stirring of 20 min at 0° C., the solution was washed with ice-cold water (8 ml for 2 times), dried on $Na_2SO_4$ and then filtered. 2,5-Di-tert-butyl-hydroquinone (0.5 mg) (polymerization inhibitor) was added to the chloroform solution, which was concentrated to a volume of 3 ml, using a rotary evaporator and filtered. Ethyl acetate (3 ml) and n-hexane (2 ml) were slowly added while stirring to the chloroform solution, which was left at 0° C. for several hours. The precipitate, a colorless solid, was separated by filtration and washed with an ice-cold solution of ethyl acetate/n-hexane (4/1) and then washed only with n-hexane.

$^{13}$C-NMR (DMSO), δ (ppm): 150 (carbonyl), 137 ($CH_2$=), 122 (—CH=), 24.8 (—$CH_2$—)

EXAMPLE 2

Synthesis of poly (N,N-dimethylacrylamide-co-N-acryloyloxysuccinimide) [DMA98-co-NAS2]

In a 25 ml, round-bottomed flask, equipped with condenser, magnetic stirring and nitrogen connection, N,N-dimethylacrylamide (600 mg, 6.15 mmol), N-acryloylsuccinimide (20.7 mg, 0.12 mmol) were dissolved in 6 ml of dry tetrahydrofuran (THF). The solution was degassed by alternating a nitrogen purge with a vacuum connection, over a 30 min period. Two mg of α,α'-azoisobutyronitrile (AIBN) were added to the solution which was then warmed to 50° C., and left at this temperature under a slightly positive nitrogen pressure for 24 hours. After the polymerization was completed, the solution was evaporated using a rotary evaporator, the white solid was dissolved in chloroform and precipitated by adding petroleum benzin. The supernatant was discarded and the whole procedure repeated 2 times. The polymer was dried under vacuum for 24 h at room temperature and stored at 4° C.

$^{13}$C-NMR (DMSO), δ (ppm): 174.6 (backbone carbonyl), 166 (succinimide carbonyl) 40-30 (metylene carbons). The degree of succinimide insertion was determined from the ratio of the integrals of backbone and succinimide carbons and it was found to be 1.5%.

EXAMPLE 3

Synthesis of [DMA90-co-NAS10]

The synthetic pathway is the same as reported above, with the only difference being the ratio of DMA (600 mg, 6.15 mmol) to NAS (103.4 mg, 0.62 mmol). $^{13}$C-NMR (DMSO), δ (ppm): 174.6 (backbone carbonyl), 166 (succinimide carbonyl) 40-30 (metylene carbons). The degree of succinimide insertion was determined from the ratio of the integrals of backbone and succinimide carbons and it was found to be 7%.

EXAMPLE 4

Synthesis of poly (N,N-dimethylacrylamide-co-N-acryloyloxysuccinimide-co-N,N,N-trimethylaminoethylacrylamide)

The synthetic path is the same as for [DMA98-co-NAS2]: N,N-dimethylacrylamide (600 mg, 6.15 mmols), N-acryloyloxysuccinimide (20.7 mg, 0.12 mmols) and N,N,N-trimethylaminoethylacrylamide (47 mg (0.3 mmols) in 6 ml of anhydrous tetrahydrofuran (THF).

EXAMPLE 5

Synthesis of poly (N,N-dimethylacrylamide-co-glycidilmethacrylate-co-acrylic acid) [DMA94-GMA2-AAc4]

In a 25 ml, round-bottomed flask, equipped with magnetic stirring and nitrogen connection, N,N-dimethylacrylamide (459 mg, 4.7 mmol), glycidilmethacrylate (14.2 mg, 0.10 mmol) and acrylic acid (14.6, 0.20 mmol) dissolved in 8.1 ml of water. The solution was degassed by alternating a nitrogen purge with a vacuum connection, over a 30 min period. One mg/µL of TEMED and 1 mg/µL of APS (from a stock solution 40% w/v) were added to the solution which was left under a slightly positive nitrogen pressure for 90 min. The solution was diluted to a final concentration of 0.5% and diluted 1:1 with a solution of ammonium sulfate at 40% of saturation immediately before use for coating preparation.

EXAMPLE 6

Assay of the active ester content of [DMAn-co-NASm], with n=98, m=2; and n=90, m=10, in aqueous solution.

N-hydroxysuccinimide showed no UV absorption at 260 nm, however,

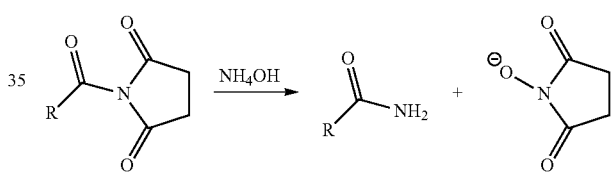

under basic conditions, an absorption peak appeared at this wavelength due to the presence of the anionic species 1, λ max=260 nm, ε=9700 $M^{-1}$ $cm^{-1}$ Therefore the appearance of 1 upon alkaline hydrolysis can be used to assess the amount of NAS incorporated into the polymers and freely accessible to the hydrolysis. The appearance of 1 was followed spectrophotometrically at 260 nm at 25° C. After the reaction was completed and the increase of the absorbance leveled off, the active ester concentration was calculated from the extinction coefficient of 1.

[DMA98-co-NAS2] and [DMA90-co-NAS10] contained respectively 90 and 400 µmol of active N-hydroxysuccinimide ester groups/g of polymer indicating that the accessible NAS groups are ~1% and 4%.

EXAMPLE 7

Assay of the Active Ester Content of [DMAn-Co-NASm], with n=98, m=2; and n=90, m=10, Grafted onto the Surface of Test Tube.

A test tube (6 cm high, 0.8 large) was coated with a solution of polymer bearing NAS groups. The determination of the NAS groups accessible to hydrolysis after adsorption of the polymer onto the surface was carried out by recording the variation of absorbance at 260 nm of an ammonia solution used to hydrolyze NAS groups on the inner surface of the test tube. Again, an increase in UV absorption at 260 nm was determined by the production of 1 upon hydrolysis.

For [DMA98-co-NAS2], the number of active NAS/mm$^2$, was 29.0 pmol/mm$^2$.

EXAMPLE 8

Glass Slides Coating

Figure 2:
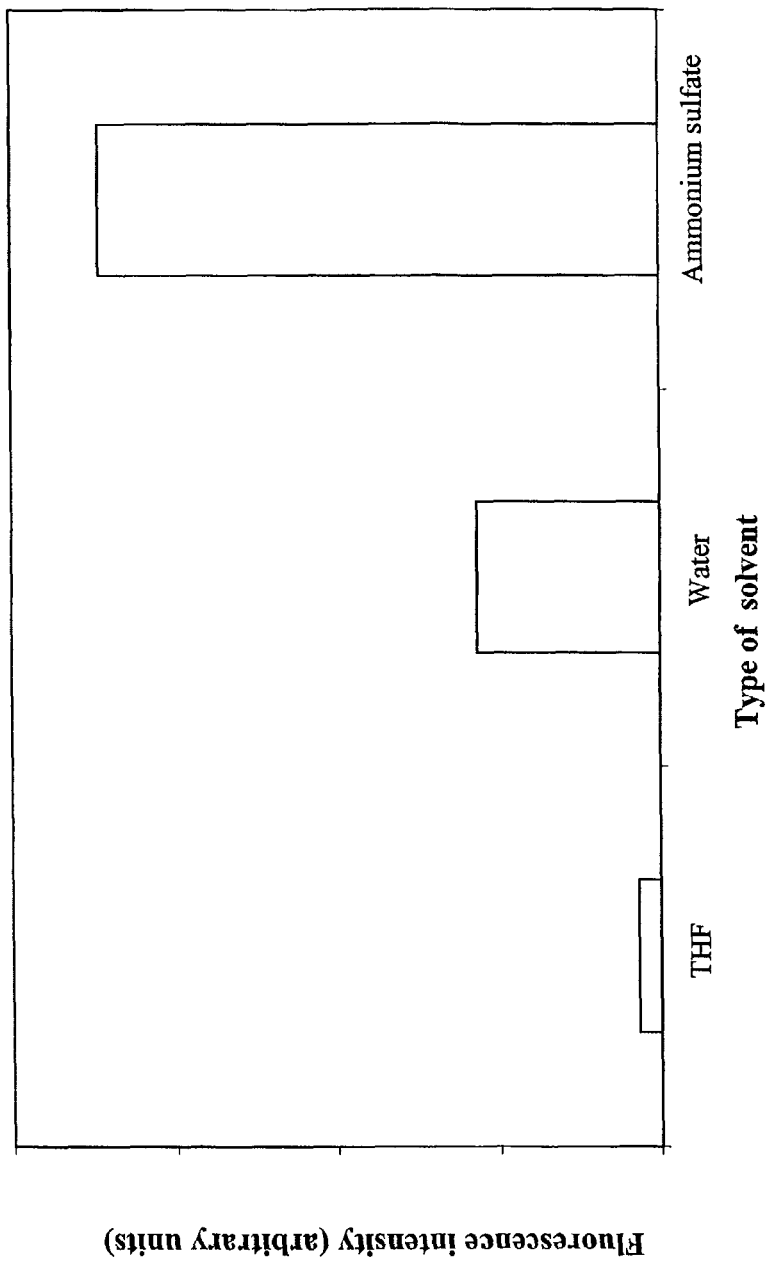
FIG. 2: Fluorescence intensity of hybridized oligonuclotides vs. solvent from which the coating [DMA98-co-NAS2] at 1% w/v concentration is adsorbed onto the slides. One nL of a 5'amino modified oligonucleotide (20 mer) was spotted at 50 µM concentration on slides coated with [DMA98-co-NAS2] dissolved at 1% w/v concentration in water, tetrahydrofuran and ammonium sulfate (20% of saturation). Oligonucleotides, spotted on different slides, were hybridized according to the protocol reported in the experimental section with the complementary probes labeled at the 3' end with Cy5 for 2 hours at 65° C. After washing, the slides were scanned with a Virtek scanner, and the images were analyzed using the Virtek ChipReader software. Each fuorescence intensity value represents an average value of 6 measurements.

Coating the glass slides requires two steps, a) surface pretreatment and b) adsorption of the polymer. In the first step the slides were washed with 1 M NaOH for 30 min, with 1 M HCl for 30 min, with water and dried. In the second step, pretreated glass slides were immersed for 30 min in a solution of polymer from 0.2 to 1% w/v dissolved in a water solution of ammonium sulfate at 20% of saturation. The slides were then washed extensively with water and dried in an oven at 60° C. Effect of polymer concentration on the fluorescence intensity after hybridization was investigated. FIG. 1 shows the fluorescence signal of hybridized oligonucleotides as a function of the polymer concentration used during the adsorbing stage. A 1% w/v polymer concentration provided the best results. Addition of ammonium sulfate to the polymer solution also improved the fluorescence signal, whereas dissolution of the polymer in an organic solvent dramatically reduced the amount of polymer adsorbed onto the surface. FIG. 2 summarize the results in terms of fluorescence signal obtained with polymer dissolved in different media.

EXAMPLE 9

Activation of slides coated with [DMA94-GMA2-AAc4] bearing a carboxylic acid as a precursor. Glass slides were coated with 0.025% polymer solution in ammonium sulfate as reported in example 8. After coating, the slides were dried under vacuum at 80° C. and subsequently immersed in a solution containing N-(3-dimethylaminopropyl)-N'-ethyl-carbodiimide, acetic acid and dimethylaminopyridine. The slides were whased with water and immersed in a solution of N-hydroxysuccinimide, rinsed with water and dried in a vacuum oven at 80° C.

EXAMPLE 10

Immobilization of Probes

Figure 3:
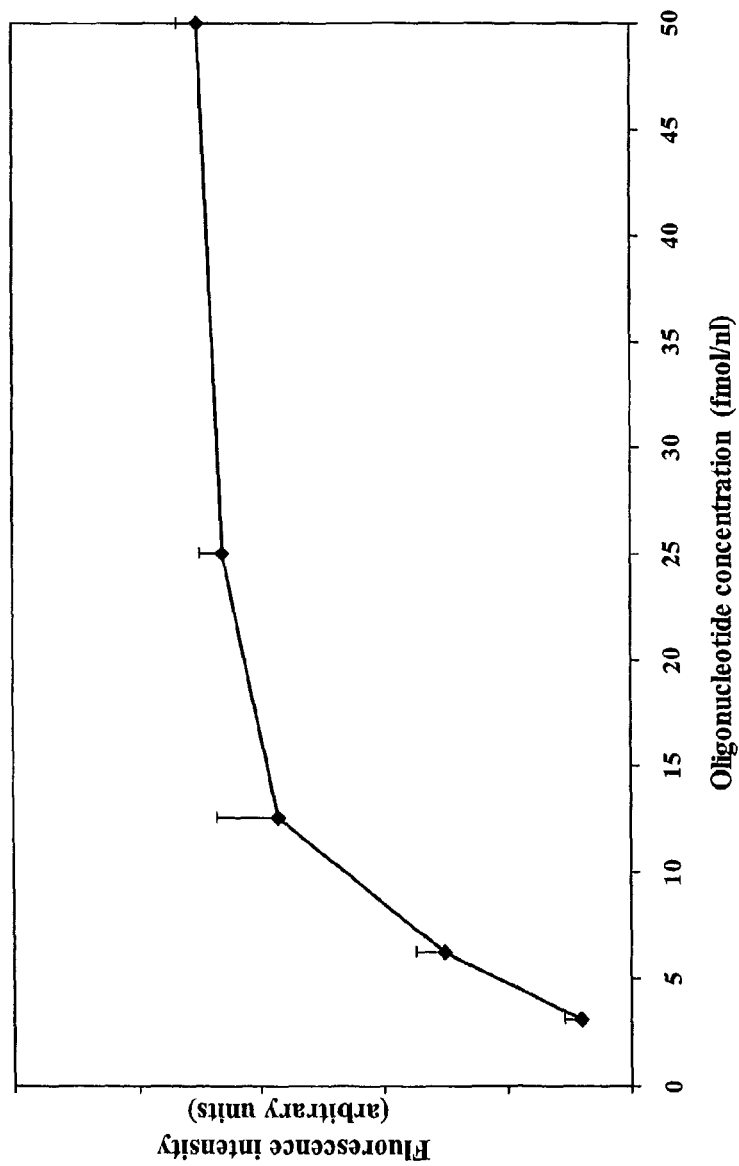
FIG. 3: Average fluorescence intensity of spots as a function of the amount of spotted oligonucleotide. One nL of a 1, 5, 25 and 50 µM solution of an amino modified oligonucleotide (20 mer) was spotted on slides coated with [DMA98-co-NAS2] dissolved at 1% w/v concentration in ammonium sulfate (20% of saturation). The spotted oligonucleotides were hybridized according to the protocol reported in the example section with target complementary oligonucleotides labeled at the 3' end with Cy5 for 2 hours at 65° C. After washing, the slides were scanned with a Virtek scanner, and the images were analyzed using the Virtek ChipReader software. Each florescence intensity value represents an average value of 6 measurements and is given in arbitrary units.

DNA deposition: custom synthesized 3'-amine-modified olionucleotides and PCR products, previously desalted, were dissolved in 150 mM sodium phosphate buffer at pH 8.5. Stock solutions 100 µM or 0.1-0.5 mg/mL were respectively used for oligonucleotieds and PCR. DNA solutions were diluted to 25, 10 and 5 µM and spots of 1 nL were printed on coated slides to form microarrays. FIG. 3 shows the fluorescence intensity of the hybrids as a function of the concentration of oligonucleotides spotted onto the surface Printed slides were placed in a storage box and the uncovered storage box was placed in a sealed chamber, saturated with NaCl, and allowed to incubate at room temperature. Overnight incubation showed the best results, the minimum incubation time was 4 hours.

Hybridization protocol: the residual reactive groups were blocked by immerging the printed slides in 50 mM solution of ethanolamine in 0.1 M Tris, pH 9.0, containing 0.1% sodiumdodecilsulfate (SDS) at 50° C. for 15 min. After discarding the blocking solution, the slides were rinsed two times with water and shacked for 15 to 60 min with 4×SSC/0.1% SDS buffer, pre-warmed to 50°. After a brief rinse with water the slides were treated in different ways depending on the nature of the probes. In the case of oligonucleotide arrays the slides were placed in the rack and centrifuged at 800 rpm for 3 min. In the case of double stranded DNA arrays, the slides were placed in boiling water for two minutes, rinsed twice with water and centrifuged at 800 rpm for 3 min. Next, the target molecules (2.5 µL per cm$^2$), were dissolved in an appropriate hybridization buffer, heated in a boiling water bath for two minutes, cooled and immediately applied to micrarrays prepared as described above. The slides, placed in a hybridization chamber were transferred to a humidified incubator at the appropriate temperature for 4-16 hours.

Figure 4:
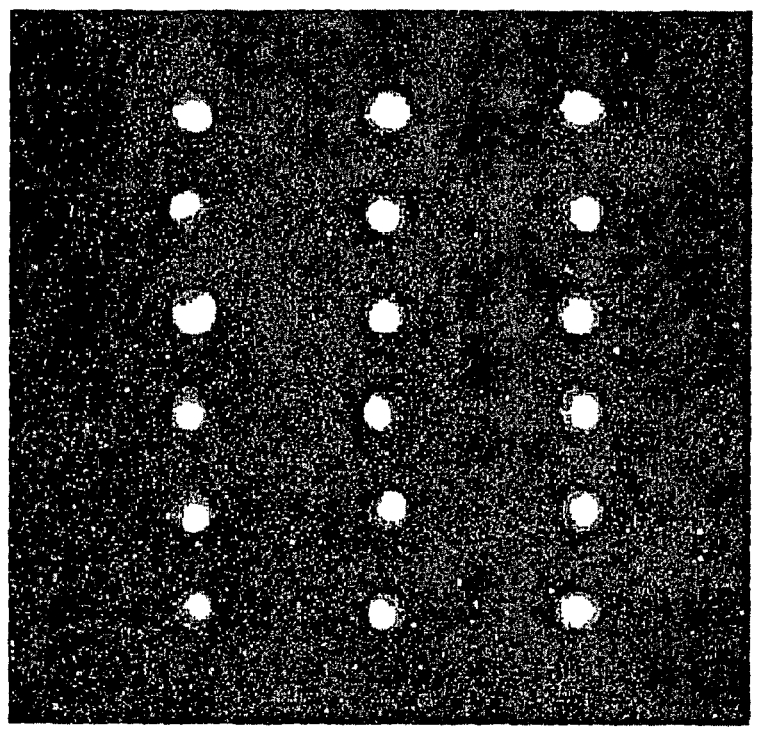
FIG. 4: Oligo-oligo, hybridization experiment: 1 nL of 5' amino-modified oligonucleotide, at 10 µM (left line), 25 µM (central line) and 50 µM (right line) concentration, was spotted onto a slide coated with a 1% w/v solution of [DMA98-co-NAS2], dissolved in ammonium sulfate (20% of saturation) and hybridized with a complementary probe according to the procedure described in the Examples, labeled with Cy5 at the 3' end for 2 hours at 65° C. After washing, the slides were scanned with a Virtek scanner, and the images were analyzed using the Virtek ChipReader software.
Figure 5:
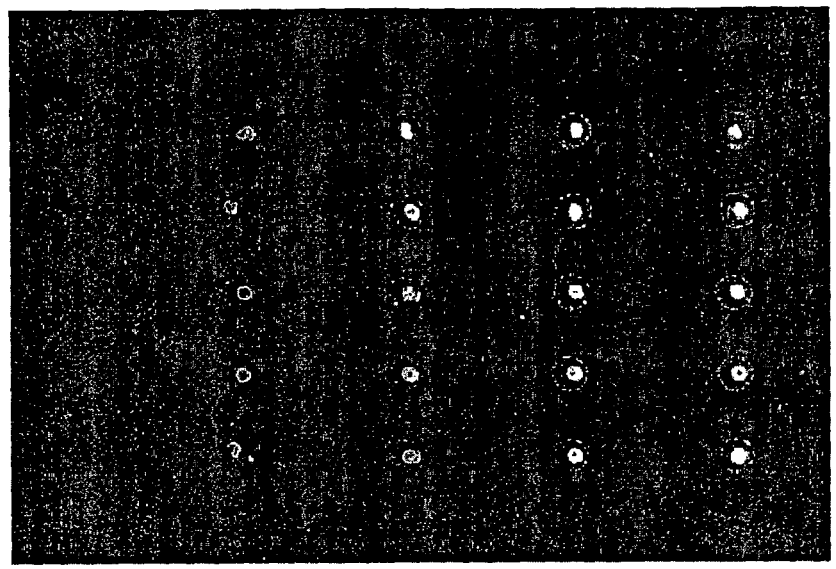
FIG. 5: oligo-cDNA hybridization experiment

Wash and scan: The slides were washed with 2×SSC/ 0.1% SDS at hybridization temperature for 5 minutes. This operation was repeated two times and was followed by two washing steps with 0.2×SSC and 0.1×SSC. The slides were dried and scanned. FIG. 4 shows the results of a hybridization experiment between oligonucleotides deposited on the surface and oligonucleotides labeled with Cy5 and compares the results with those obtained with a commercial slides under identical conditions.

The invention claimed is:

1. A water soluble copolymer for the covalent binding and immobilization of biological molecules onto a solid support, the copolymer comprising at least the following different copolymerized monomer repeat units:
   (a) a copolymerized acrylamide or methacrylamide monomer repeat unit which provides for adsorption of the copolymer to the surface of the solid support, wherein the acrylamide or methacrylamide is di-substituted on the nitrogen by C1-C12 linear or branched alkyl chains, which in turn can be substituted by a halogen, or by a methoxy;
   (b) a copolymerized ethylene or acrylic monomer repeat unit comprising functional groups able to covalently bind biomolecules, wherein said functional groups are succinimide, maleimide, oxirane, or carboxylic acid; and
   (c) a copolymerized ethylene monomer having functional groups different from said functional groups in (b) and is able to covalently react with glass silanols,
   wherein the copolymer is soluble in water in an amount of at least 0.1 wt. %, and wherein the copolymer is adapted for the covalent binding and immobilization of biological molecules when adsorbed onto the solid support,
   wherein the monomer repeat unit (a) is present in at least 90 mole percent with respect to the monomer repeat units (a), (b), and (c).

2. The copolymer of claim 1, wherein the monomer repeat unit (a) is selected from acrylamide or methacrylamide which is di-substituted on the nitrogen with methyl.

3. The copolymer of claim 1, wherein the monomer repeat unit (a) is dimethylacrylamide.

4. The copolymer of claim 1, wherein the functional group for monomer repeat unit (b) is succinimide or maleimide.

5. The copolymer of claim 1, wherein the monomer repeat unit (b) is N-acryloyloxy succinimide.

6. The copolymer of claim 1, wherein the monomer repeat unit (a) is dimethylacrylamide and the monomer repeat unit (b) is N-acryloyloxy succinimide.

7. The copolymer of claim 1, wherein for the monomer repeat unit (c) the groups are able to react with a glass solid support having surface silanols.

8. The copolymer of claim 1, wherein the monomer repeat unit (c) bears the epoxy functional group.

9. The copolymer of claim 1, wherein the monomer repeat units (c) bear glycidyl functional group.

10. The copolymer of claim 1, wherein the biological molecules are peptides, proteins, or DNA.

11. An aqueous solution comprising water and the copolymer according to claim 1.

12. The aqueous solution of claim 11, wherein the aqueous solution contains 0.1 to 20% of said copolymer.

13. The aqueous solution of claim 11, wherein the aqueous solution contains ammonium sulfate.

14. The aqueous solution of claim 11, wherein the aqueous solution contains 20% saturation ammonium sulfate.

15. A solid support for biological molecules having at least one surface coated with the copolymer according to claim 1.

16. A solid support according to claim 15, wherein the solid support is selected from multi-well plates, beads, tubes, microscope slides, wafers, and silica membranes.

17. A method for coating a solid support surface, which comprises contacting an aqueous solution of the copolymer according to claim 11 with the surface for a time sufficient for the co-polymer to adsorb on the solid surface.

18. A method according to claim 17, wherein the aqueous solution further comprises ammonium sulfate.

19. A water soluble copolymer for the covalent binding and immobilization of biological molecules onto a solid support, the copolymer comprising at least the following different copolymerized monomer repeat units:
 (a) a copolymerized acrylamide or methacrylamide monomer repeat unit which provides for adsorption of the copolymer to the surface of the solid support, wherein the acrylamide or methacrylamide is di-substituted on the nitrogen by C1-C12 linear or branched alkyl chains, which in turn can be substituted by a halogen, or by a methoxy;
 (b) a copolymerized ethylene or acrylic monomer repeat unit comprising functional groups able to covalently bind biomolecules, wherein said functional groups are succinimide, maleimide, oxirane, or carboxylic acid, and wherein said functional groups are introduced after copolymerization; and
 (c) a copolymerized ethylene monomer having functional groups different from said functional groups in (b) and is able to covalently react with glass silanols,
 wherein the copolymer is soluble in water in an amount of at least 0.1 wt. %, and wherein the copolymer is adapted for the covalent binding and immobilization of biological molecules when adsorbed onto the solid support,
 wherein the monomer repeat unit (a) is present in at least 90 mole percent with respect to the monomer repeat units (a), (b), and (c).

* * * * *